United States Patent [19]

DuBois

[11] 4,402,990
[45] Sep. 6, 1983

[54] STEVIOLMONOSIDE ANALOGS

[75] Inventor: Grant E. DuBois, Palo Alto, Calif.

[73] Assignee: Dynapol, Palo Alto, Calif.

[21] Appl. No.: 296,568

[22] Filed: Aug. 26, 1981

[51] Int. Cl.³ .................. C07H 15/24; A23L 1/236
[52] U.S. Cl. ............................... 426/658; 536/18.1; 426/548
[58] Field of Search .............. 426/548, 658; 536/4, 536/18.1

[56] References Cited

U.S. PATENT DOCUMENTS 3,876,816  4/1975  Zaffaroni ........................ 426/548
4,082,858  4/1978  Morita et al. .................. 426/658 X
4,226,804  10/1980 DuBois et al. ................. 426/548 X
4,332,830  6/1982  DuBois ........................... 426/658

Primary Examiner—Joseph M. Golian
Attorney, Agent, or Firm—Burns, Doane, Swecker & Mathis

[57] ABSTRACT

Analogs of the glycoside stevioside are disclosed. These materials have the formula

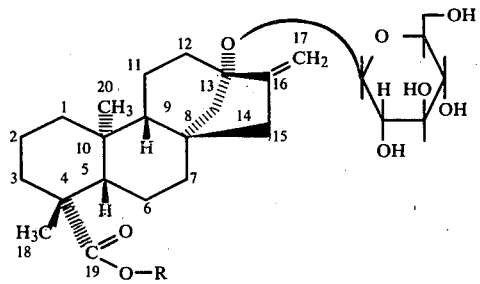

wherein R is a simple physiologically acceptable non-carbohydrate polar organic group. The analogs are sweet and find use as sweeteners.

17 Claims, No Drawings

STEVIOLMONOSIDE ANALOGS

BACKGROUND OF THE INVENTION

1. Field of the Invention

This invention relates to chemical analogs of steviolmonoside which are formed from the sweet glycoside, stevioside; which are themselves sweet and useful as sweeteners; and which do not degrade under conditions of use to form physiologically undesirable steviol as do stevioside and steviolmonoside.

2. The Prior Art

The leaves of the Paraguayan shrub *Stevia rebaudiana* Bertoni have long been known to be sweet. A sweet crystalline glycoside has been isolated from these leaves. This compound, named stevioside by the Union International de Chimie in 1921, has been reported to be about 300 times as sweet as sucrose by Bridel et al., *Compt. Rend.*, 192, 1123-5 (1931) and *J. Pharm. Chim.*, 14(3), 99-113; 14 (4),154-161 (1931). Mosettig et al. reported the absolute configuration of stevioside as shown in general formula I.

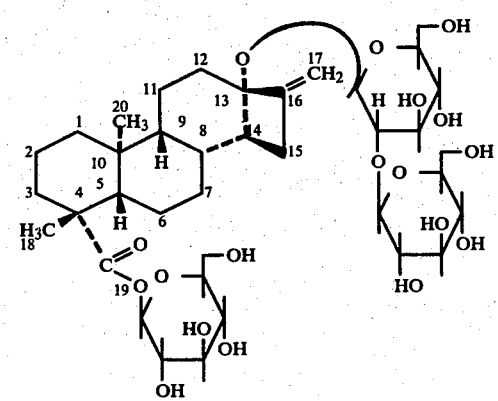

in *J. Am. Chem. Soc.*, 85, 2305-2309 (1963). This material has attracted substantial interest as a potential sweetener, particularly in the orient where its plant source is now cultivated and where crude stevioside-containing extracts are used as sweeteners. (see Japanese Pat. Nos. 51-52200; 52-47956, 7 and 9; 52-51069; 52-57198 and 9 and 52-62300.)

Tanaka, et al., have shown in *Chem Pharm Bull* 25, 2466-7 (1977) that stevioside undergoes selective enzymatic conversion to steviol-13,19-bioside (II) in the presence of Takadiastase Y. This material can be converted to steviolmonoside (III) by treating with base.

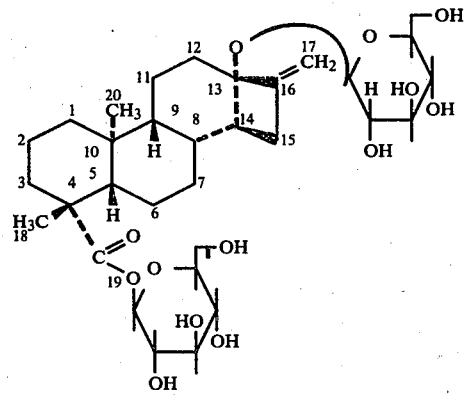

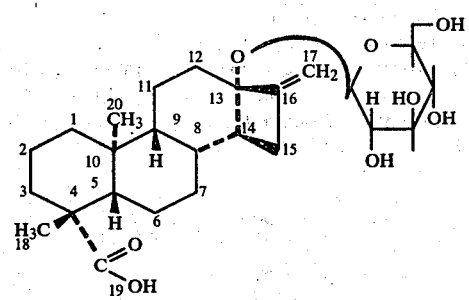

Stevioside's acceptance in the United States has been slow. Possibly, this is because its sweet taste is contaminated by a substantial degree of bitterness. (Bridel et al., above). It also may be due to concerns about the compound's safety.

In 1966, P. V. Vignais and coworkers reported the results of a study concerned with elucidation of the mode of action of the respiratory toxin, atractyligenin. Included in their study were several compounds of related structure including steviol (IV), the aglycone of stevioside and steviolmonoside.

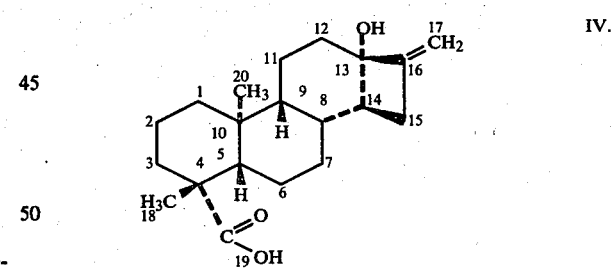

Surprisingly, in cell mitochrondria, steviol was found to be an even more potent inhibitor of ATP synthetase than atractyligenin. (*Biochim. Biophys. Acta*, 118, 465-483 (1966).) In addition, steviol is reported to exhibit antiandrogenic effects (Dorfman, R. I., et al., *Endocrinology*, 67, 282-285 (1965)). Clearly, if stevioside was converted to steviol in vivo, significant toxicity may be expected. Recent results suggest the likelihood that stevioside or steviolmonoside would be largely converted to steviol in vivo, and further that the steviol thus produced would subsequently be completely absorbed through the gastrointestinal tract wall. (R. Wingard, J. Dale, J. Brown, R. Hale, *Experientia*, 36, 519, (1980)). Thus, as a result of a combination of the Vignais and Wingard work, it may be concluded that, with widespread use, stevioside may be expected to exhibit significant acute toxicity. If, however, stevioside's metabolism to steviol could be prevented, that is if a potently sweet analog could be developed which was not degraded to steviol, safety for use in foods would be anticipated.

REFERENCE TO RELATED APPLICATION

On Sept. 22, 1980, U.S. patent application Ser. No. 189,243 was filed. This application has now issued on June 1, 1982 as U.S. Pat. No. 4,332,830. It also relates to G.I. tract-stable stevioside analogs but its compounds have only the naturally occurring β-D-sophorosyl disaccharide moiety attached to the C-13 hydroxyl group.

STATEMENT OF THE INVENTION

A family of new chemical analogs of stevioside has now been discovered based on steviolmonoside. These materials are useful as sweeteners and unexpectedly have the property of being stable to mammalian gastrointestinal tract conditions and not generating steviol in vivo. These compounds have the chemical structures of formula V

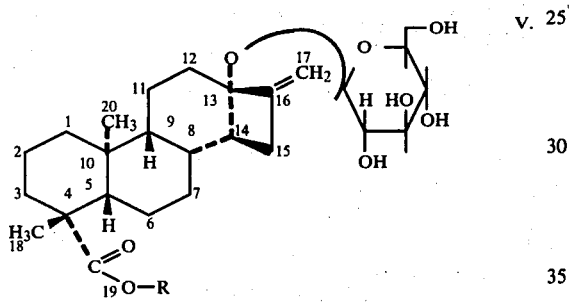

wherein R is a simple noncarbohydrate polar group. These compounds may be further classified as nonglycosidic polar esters of steviolmonoside.

In another aspect, this invention involves the use of these new compounds as sweeteners for comestibles wherein they are admixed with said comestibles.

DETAILED DESCRIPTION OF THE INVENTION

The Compounds

In this Description of the Invention reference will be made to a variety of related diterpenoid compounds. These compounds include:

| | |
|---|---|
| Stevioside | the natural product shown in general formula I |
| Steviol-13,19-bioside | the enzyme cleavage product shown in general formula II. |
| Steviolmonoside | the base hydrolysis product of steviol-13,19-bioside shown in general formula III. |
| Steviol | the aglycone of stevioside shown in general formula IV |
| Steviolmonoside esters | the compounds shown in general formula V wherein "R" is as defined. |

The compounds of this invention differ structurally from art-known stevioside and steviolmonoside in the nature of the "R" substituent attached to the C-19 oxygen. In the present material, R is a physiologically acceptable noncarbohydrate polar organic group. R should not have oxygen substituted on its α-carbon, that is, it should be α-carbon oxygen free as such substitution in this position is equivalent to acetal functionality which is unstable in vivo and could lead to "R-group" cleavage and formation of steviol. The α-carbon can be substituted with carboxyl, sulfo, phospho, and similar polar groups, however.

R may preferably be selected from among 1 to 10 carbon atom polar organic groups. Preferably, R has from 2 to about 5 carbon atoms. Of necessity, these polar groups will include atoms beyond carbon and hydrogen such as the heteroatoms oxygen, sulfur, nitrogen and phosphorous. These heteroatoms may form anionic or cationic or zwitterionic polar moieties including sulfonate, sulfamate, carboxylate, and phosphonate anions, ammonium cations and combinations thereof. These polar moieties are accompanied by physiologically acceptable counterions. Representative R groups include the materials listed in Table I. Table I also lists precursors or precursor sequences which can be used to insert these R groups as will be set forth herein as Preparative Methods.

TABLE I

| R GROUP | Precursors |
|---|---|
| 1-5 carbon alkyl terminal sulfonates. —(CH$_2$)$_n$—SO$_3^-$M$^+$* n = 1-5, preferably 2-5, more preferably 3 or 4 and most preferably 3 | Br—(CH$_2$)$_n$—SO$_3^-$M$^+$ 1,3-Propane sultone 1,4-Butane sultone |
| 1-5 carbon alkyl polysulfonates (preferably 2-5 carbons) —CH$_2$—CH—(SO$_3^-$M$^+$)$_2$ —(CH$_2$)$_2$—CH—(SO$_3^-$M$^+$)$_2$ —CH$_2$—CH(SO$_3^-$M$^+$)—CH$_2$—SO$_3^-$M$^+$ | Br—(CH$_2$)$_2$—CH(SO$_3^-$M$^+$)$_2$ ![structure with (CH$_2$)$_n$, SO$_2$, SO$_2$, phenol-OH] Etc.  n = 1,2 |
| 1-5 carbon alkyl terminal carboxylates —(CH$_2$)$_n$—COO$^-$M$^+$ n = 1-5 preferably 1-3 | Br—(CH$_2$)$_n$—COOGp* |
| 1-5 carbon alkyl polycarboxylates | Br—CH—(COOGp)—(CH$_2$)$_2$—COOGp |

TABLE I-continued

| R GROUP | Precursors |
|---|---|
| —CH(COO⁻M⁺)—(CH₂)₂—COO⁻M⁺ Etc. | |
| 1-5 carbon alkyl terminal phosphonates —(CH₂)ₙ—PO₃H⁻M⁺ n = 1-5, preferably 2-4 | Br—(CH₂)ₙ—PO₃(Gp)₂ |
| 1-5 carbon polyols | 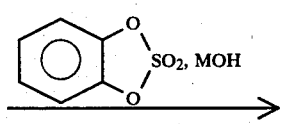 |
| (CH₂)ₙ̄CH(OH)—CH(OH)—CH₂OH | |
| (CH₂)ₙ̄CH(OH)—CH₂OH Etc. n = 1,2 | |
| 1-5 carbon primary amine salts —(CH₂)ₙ—NH₃⁺X⁻* n = 1-5, preferably 2-4 | |
| 1-5 carbon alkyl sulfamates —(CH₂)ₙ—NH—SO₃⁻M⁺ n = 1-5, preferably 2-4 | |
| 1-5 carbon alkyl amino-carboxylates —(CH₂)ₙ—CH(NH₃⁺)—COO⁻ n = 1-4, preferably 2-3 | |
| —(CH₂)ₙ—CH(COO⁻)—(CH₂)ₘ—NH₃⁺ n = 1-2, m = 1-3 | |

*M⁺ = physiologically acceptable alkali metal cation, or alkaline earth metal cation particularly Na⁺, K⁺, Mg⁺⁺ or Ca⁺⁺
*X⁻ = physiologically acceptable anion such as Cl⁻
*Gp = protecting group, e.g. —CH₃, or —C₂H₅, or the like that protects a labile functionality and is thereafter removed.

These R groups are merely representative. For example, straight chain ester substituents have been shown Among the compounds of this invention preference is given those having 1–5 carbon alkyl terminal sulfonate R groups while among these, the compounds wherein R is —(CH$_2$)$_3$—SO$_3^-$K$^+$ or (CH$_2$)$_3$—SO$_3^-$Na$^+$ are more preferred. These two most preferred compounds can be named as steviolmonside, sulfopropyl ester, potassium and sodium salts.

Preparative Methods

The compounds of the invention can be prepared from commercially available stevioside by the general preparative scheme of (a) cleaving a glucose from stevioside to form steviol-13,19-bioside using the above-noted enzymatic procedure of Tanaka et al (expressly incorporated herein by reference), (b) saponifying this intermediate to produce steviolmonoside, and (c). then reacting steviolmonoside with an "R-addition" reagent, that is a reagent that will add the desired R to the steviolmonoside in place of the hydrogen atom of steviolmonoside's C-19 carboxyl.

More particularly, the enzyme cleavage is carried out by dissolving in a liquid medium and incubating the stevioside with from about 0.25 to 5.0 times its weight of the enzyme takadiastase Y or its equivalent. Other suitable enzymes include naringinase, various β-amylases, and mixed glycosidases from sources such as *Corona lampas, Turbo cornutus* and *Helix pomatia*. Preferably the amount of enzyme is from 0.5 to 3 times and more preferably about 1 to 2 times the weight of stevioside. The liquid medium is an aqueous mildly acidic broth. A typical broth is sterile buffered aqueous citric acid made up from citric acid and an alkali metal hydrogen phosphate with a molarity of 0.05 to 0.4 and a pH of 3.5 to 6, especially 4 to 5. The stevioside concentration is from 0.2 to 20 mg/ml, preferably 0.5 to 5 mg/ml in the broth.

The reaction proceeds at ambient or mildly elevated temperatures such as 10° to 50° C., especially 25° to 45° C. and generally requires several days (such as 3 to 10 days) to reach completion. Usually, one monitors the reaction progress by thin layer chromatography or the like and continues it to completion.

Following the cleavage, an isolation/purification step is usually carried out. This is done by crystallization, extraction or preferably by column chromatography such as silica gel absorption chromatography with subsequent recovery of the steviol-13,19-bioside from the column eluent.

The saponification is carried out by reacting the steviol-13,19-bioside with a molar excess (at least 5 equivalents) of a strong base, especially aqueous or alkanolic or mixed aqueous-alkanoic KOH or NaOH and particularly aqueous and/or methanolic KOH, at elevated temperatures such as from 50° C. to 150° C., preferably from 60° to 100° C. for a time adequate to affect essentially complete saponification. An especially preferred reaction uses 40–80% methanol as a cosolvent as this gives an easily filtrable granular product. At atmospheric pressure this reaction is best carried out at about 65° C., the boiling point of methanol. The concentration of the base is generally from about 1%wt to about 20%wt. The time required would be in the range of from 0.1 hours to 3 hours and would depend upon the temperature employed. At higher temperatures, say 100°–150° C., times from 0.1 to 1 hour are preferred. At lower temperatures, say 50°–100° C., times from 1 to 3 hours are preferred.

Following saponification, the reaction medium is generally neutralized, such as with mineral acid, and the steviolmonoside is recovered. This recovery can be effected by crystallization, brought about by cooling or removal of solvent. The steviolmonoside can be purified by recrystallization, column chromatography or a like process at this point. Such a purification is generally performed.

The steviolmonoside (preferably recovered and purified) is contacted with the "R-addition" agent, under mildly basic conditions to effect addition. The particular "R-addition" agent employed of course depends upon the "R" group sought to be added. A list of exemplary R-addition agents is provided in Table I. In general, any reagent that will displace the steviolmonoside carbonyl groups hydrogen with R, can be used. About 1 equivalent of R-addition agent is used per equivalent of steviolbioside (preferably 0.9 to 1.1 equivalents). A weak inorganic base, such as an alkali metal or alkaline earth metal carbonate, corresponding to the counterion of the final product (if any), is present in an amount about equal to the equivalents of R-addition agent. This reaction is conducted at a low to moderate temperature (0° C. to 30° C., preferably 10°–25° C.) for an extended period such as from 4 to 48 hours especially 12 to 48 hours. This reaction is carried out in liquid phase in an aprotic reaction medium, such as dimethylformamide, N-methylpyrrolidone, acetone, dimethyl sulfoxide and the like.

Following reaction with the R-addition agent and neutralization with acid, the product is recovered such as by evaporation, followed by recrystallization. Other equivalent recovery and purification processes may be employed.

These preparative conditions are merely representative. Other equivalent routes may be employed if desired.

Stability of Compounds

An important property of these steviolmonoside R esters is their stability and resistance to conversion to steviol at the conditions of the mammalian gastrointestinal tract. This property is demonstrated in vitro by anaerobically incubating the compounds of the invention with fresh rat cecal contents for three days at 37° C. as detailed in Example 1. At these conditions, no degradation to steviol would be expected to occur to a limit of detection of 0.13%. This is based on studies with similar steviolbioside R esters which do not give up their R groups under these conditions. In direct contrast, as reported in the *Experientia* paper of Wingard, et al., noted above, stevioside itself undergoes essentially quantitative degradation to steviol and steviolmonoside would be expected to degrade to steviol, as well.

Use of the Compounds

The compounds of this invention are useful as sweeteners for comestibles. In this application, they are simply admixed with the comestible by art-known means in dry form or as solutions, preferably in water. They are, advantageously, soluble in water at usual use levels. Representative comestibles include beverages such as sodas, coffee, lemonade, wine and the like; edibles such as gelatin desserts, candy, gum, cakes, cereals and the like, personal products such as mouth wash and toothpaste as well as pharmaceuticals such as cough syrups, and flavored pills.

The compounds of this invention are about 100 to 200 times as sweet as sucrose on a weight basis. Accordingly, the amounts to be employed may be determined by factoring usual sucrose use levels by this 100–200 value. Thus, for example, a soft drink might be sweetened by adding 0.05 to 0.15% by weight of the present compounds. Mixtures of these materials alone or with known other sweeteners (sucrose, saccharin or the like) may also be advantageously employed.

The invention will be further described by the following Examples. These are provided solely to illustrate the invention and are not to be construed as limiting its scope.

EXAMPLE I

Preparation of steviolmonoside, 3-sulfopropyl ester, potassium salt

A. Stevioside Purification

Stevioside was isolated from a crude material assayed to contain 88% stevioside, 3% rebaudioside A, and 9% steviolbioside. Ten grams of this crude sweetener was dissolved with heating in 400 ml boiling absolute ethanol. Crystallization over 60 h at ambient temperature followed by filtration and drying in vacuo yielded 5.44 g of tiny colorless clusters. Karl Fischer titration showed this sample to be anhydrous while high performance liquid chromatography (30 cm C-18 on μ-Bondapak; 10–40% MeCN in 0.005 M $KH_2PO_4$; 2.0 ml/min; 15 min linear program; 200 nm) showed this sample to be 97.5% stevioside and 2.5% steviolbioside.

B. Enzyme Treatment

A 4.604 g sample of the recrystallized stevioside was incubated for 8 days with 4.605 g Takadiastase Y (Sanzyme R) in 460 ml of a pH 4.05 broth made up of 61 volume % 0.1 M citric acid and 39 volume % 0.2 M $Na_2HPO_4$ at 37° C. Periodic samples were taken and analyzed by thin layer chromatography for disappearance of starting material and appearance of new product. During incubation a large amount of white precipitate formed. At the end of the incubation, the slurry was diluted to 800 ml with distilled water. The mixture was then extracted thrice with n-butanol. The extracts were then evaporated and the solid dissolved in methanol and recrystallized. The major component of the recrystallized product was steviol-13,19-bioside (Compound II). The recrystallized product of this and a duplicate run were then combined and chromatographed over 500 g silica gel (60–200 mesh) eluting with $CHCl_3$–$CH_3OH$ mixtures. Combination of pure fractions gave 5.14 g (70%) of steviol-13,19-bioside.

C. Saponification to Steviolmonoside

Steviol-13,19-bioside (4.33 g; 5.5 mmol) was added to 95 ml of 10% NaOH and 95 ml of methanol in a 500 ml flask. After flushing with argon, the mixture was heated to reflux. After 1.5 hours, the reaction mixture was cooled to 5° C., and brought to pH 3.3 with 50% $H_2SO_4$. A solid precipitate formed. This mixture was extracted with EtOAc (4×50 ml), the combined portions of which were dried over $MgSO_4$ and concentrated to dryness to yield the colorless solid.

The solid was dissolved and recrystallized from methyl ethyl ketone/methanol. The resulting solid tan-white prisms were washed with neat methylethyl ketone and vacuum dried to yield 1.156 g of product which by TLC and HPLC analysis was found to be homogeneous.

D. R-agent Addition

A mixture of (0.98 mmole) steviolmonoside, 471 mg, (1.179 mmol) 1,3-propane sultone, 144 mg, (1.078 mmole) potassium carbonate, 149 mg, and 7 ml DMF was stirred vigorously at ambient temperature under an inert atmosphere for 21 hours. TLC analysis (Silica Gel F-254; $CHCl_3$—MeOH—$H_2O$/15-10-2) showed one product (Rf=0.32) and the absence of starting material. The reaction mixture was treated with 0.42 ml warm 10% KOH (16 h), neutralized (HCl) and concentrated to dryness in vacuo. Desalting (Bio Rad AG 11A8 ion retardation resin), followed by silica gel chromatography ($CHCl_3$—MEOH—$H_2O$) and lyophilization yielded 494 mg (81%) of a flocculent white solid.

E. Stability Test

If Steviolmonoside, 3-sulfopropyl ester, sodium salt prepared in Part D. would be incubated anaerobically for three days at 37° C. with 5 wt% fresh rat cecal contents, at concentrations of 0.25, 0.5, and 1.0 mg/ml in sterile Krebs-Ringer 0.25 M phosphate buffer (pH 7.4) containing 0.25 mg/ml dithiothreitol and 0.25 mg/ml α-D-glucose, TLC [silica gel F-254; $CHCl_3$:$CH_3OH$:$H_2O$ (15:10:2)] and HPLC [30 cm C-18 on μ-Bondapak; 15 min linear gradient of 10–40% $CH_3CN$ in 0.005 M $KH_2PO_4$ (pH 3.45); 200 nm] analysis would show all the initial ester (Rf=0.37; $t_R$=14.6 min) to have been consumed within 24 h to yield apparently only the sulfopropyl ester of steviol, ($R_f$=0.63; $t_R$=16.3 min). No steviol ($R_f$=0.95; $t_R$=31.3 min) would be detected. Thereafter the bacterial cells would be sedimented by centrifugation. The sediment would be extracted (THF), as would the supernatant, after lyophilization. HPLC analysis for steviol of the two THF extracts should show none to be detectable, with a detection limit of 0.5 μg.

As has been shown above, the sulfopropyl ester moiety is quite stable to the biological conditions which readily degrade the glycosyl ester of stevioside.

F. Taste Test

Steviolmonoside, 3-sulfopropyl ester, potassium salt prepared in Part D. was dissolved in distilled water at a concentration of 0.05 wt% and tasted by a group of volunteers. The solution had a very intense sweet taste. It had a sweetness equivalent to 8–9 wt% sucrose, dependent on the taste tester. The taste was very sucrose-like, having negligible off-flavors.

G. Use in Comestibles

Based on the results of Part F, one can employ the compound of Part D as a sweetener for comestibles. In exemplary uses 0.10% by weight of the compound is dissolved in an unsweetened cola beverage, a like concentration of the compound is added to an unsweetened lemonade and to coffee. In each case, sweetness is imparted. In two other cases, 0.04% by weight is added to coffee along with 0.02% by weight of saccharin and 3% by weight of sucrose, respectively. Again, sweetness is imparted by the compound of Part D.

EXAMPLE II

The preparation of Part D of Example I is repeated with one change. In place of potassium carbonate, sodium carbonate is employed. This forms steviolmonoside, 3-sulfopropyl ester, sodium salt. The identical product could be achieved using an ion exchange resin to replace $K^+$ with $Na^+$, similarly ½ $Ca^{++}$ or ½ $Mg^{++}$ could replace $K^+$. When this material is evaluated, as in Parts E, F and G of Example I, it exhibits the same advantageous properties observed with the material of Example I.

EXAMPLE III

Preparation of steviolmonoside, 4-sulfobutyl ester, sodium salt

B. Steviolmonoside (2 mmol) is placed in a 50 ml round bottom flask. DMF (30 ml) is added as is 2.2 mmol of NaH. This mixture is slurried under argon until foaming ceases. Then 2.2 mmol of 1,4-butanol sultone is added. The mixture is stirred at 30°–35° C. for several days, periodically checking for reaction completeness by TLC and periodically adding an additional 1.1 mmol of NaH and 1.1 mmol of 1,4-butane sultone. A product forms and is isolated, following hydrolysis of excess sultone with warm aqueous NaOH, neutralization with 10% $H_2SO_4$, concentration to dryness, removal of salts on Bio Rad AG 11A8 ion retardation resin and recrystallization from wet ethanol.

EXAMPLE IV

Preparation of a compound wherein $R = -CH_2-CH_2-NH_3^+Cl^-$

Steviolmonoside (1 mmole) and $K_2CO_3$ (2 mmol) are added with 10 ml of distilled DMF to a 25 ml flask under argon. 1,2-dibromoethane (10 mmol) is then added and the mixture stirred at 35°–50° C. overnight. This yields steviolmonoside 2-bromo ethyl ester. This material is mixed with 40 mmol of $NaN_3$ and stirred overnight at about 25° C. to convert to the 2-azidoethyl ester. This reaction product was added to 50 ml of 1% HCl to give a precipitate that is recovered by filtration, and dried. This dry product (0.2 mmol) is dissolved in 10 ml $CH_3OH$, 10 ml THF and 1.5 ml $CHCl_3$ and mixed with 13 mg of 5% Pd on $BaSO_4$. Hydrogen is bubbled through the reaction at 5° C. overnight. Later the reaction mixture is warmed to room temperature and an additional 13 mg of catalyst is added. This gives steviolmonoside, 2-aminoethyl ester, hydrochloride.

EXAMPLE V

Preparation of compound wherein R equals $-CH(COOH) CH_2-CH_2-COOH$

Steviolmonoside (5 mmol) is dissolved in 20 ml of dry DMF under argon. $K_2CO_3$ (6.2 mmol) is added with 20 ml DMF. and 6.2 mmol of $Br-CH(COOCH_3)-CH_2-CH_2-COOCH_3$. The mixture is left to stir at room temperature for several days, and worked up by ice water addition, HCl addition (to pH 6.5) solvent evaporation, followed by silica gel column chromatography using $CHCl_3$—MeOH as eluent. A product wherein $R=-CH(COOCH_3)-CH_2-CH_2-COOCH_3$ is recovered and hydrolyzed in 50 ml of methanol and 50 ml of 10% KOH, neutralized with HCl, filtered and, the desired product recrystallized from acetone:methanol 100:1.

EXAMPLE VI

Preparation of compound wherein R equals $CH_2-CH_2-CH(NH_3^+)-COO^-$

The "R-addition agent,"

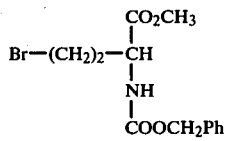

was obtained as shown in Example I of DuBois et al. U.S. Pat. No. 4,226,804 which is incorporated by reference.

Stevolmonoside (2.0 mmol), $K_2CO_3$ (2.5 mmol) and R addition agent (2.5 mmol) are placed in a flask with 25 ml of dry DMF under argon and stirred at room temperature overnight. The product is extracted with ethylacetate. The extracts are washed, dryed and evaporated to yield a solid product.

The solid product is then dissolved in 30 ml of methanol and 30 ml of 10% NaOH and heated to reflux. It is refluxed until no starting material was left by HPLC. The methanol is then evaporated and the remaining product titrated to pH 6.0 with 2 N $H_2SO_4$, and then evaporated to dryness. The solid is extracted with boiling methanol and the extracts concentrated to yield the desired solid product.

EXAMPLE VII

Preparation of Compound where R is $-CH_2-COONa$

A. Steviolmonoside (2.0 mmol), $K_2CO_3$ (2.5 mmol) and 20 ml of dry DMF are placed in a flask under argon and mixed into solution. Ethyl chloroacetate (2.5 mmol) was added and the mixture was stirred at 43° C. for five hours. It is added to excess chilled 5% HCl whereupon a precipitate formed that was recovered by filtration. This product has as its C-19 oxygen substituent, $-CH_2-CO_2-C_2H_5$.

B. The ethyl protecting group is hydrolyzed by treatment with 10% KOH until TLC assay shows reaction completion. The product is precipitated on acidification (10% HCl) to pH3 and is isolated by filtration. The product is dissolved in 1.00 equivalent 1.00 M NaOH and the resultant solution lyophilized. Recrystallization (MeOH) yields the desired steviolmonoside, carboxymethyl ester, sodium salt.

EXAMPLE VIII

It will be appreciated that the sweeteners of the invention can be incorporated into a wide range of comestibles.

Cups of coffee are prepared: To each is added 500 ppm by weight, basis solution, of one of each of the sweeteners prepared in Examples I–VII. The coffees present a sweetened taste when sampled.

Gelatin, food color and fruit flavor are dissolved in water at levels suitable for forming a jelled food product. The solution is not sweet. The materials of Examples I–VI are each added to separate samples in amounts of 600 ppm and the samples are cast into jelled products. The resulting gelatin products are sweet.

What is claimed is:

1. A stevioside analog compound having the structure

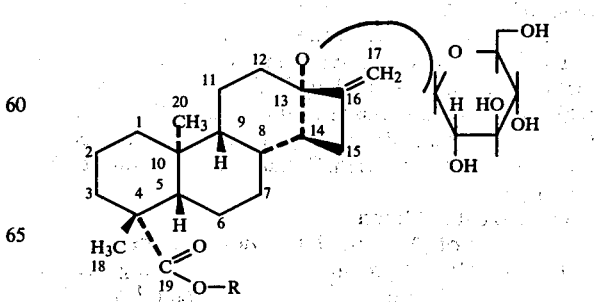

wherein R is a physiologically acceptable noncarbohydrate polar organic group.

2. The compound of claim 1 where R is α-carbon oxygen free and contains from 1 to 10 carbon atoms inclusive.

3. The compound of claim 2 wherein R's contains one or more polar moiety selected from sulfonate, sulfamate, carboxylate, and phosphonate anions, ammonium cations and hydroxyl groups.

4. The compound of claim 3 wherein R is a 1 to 5 carbon inclusive alkyl terminal sulfonate salt.

5. The compound of claim 4 wherein R is of the formula $$-(CH_2)_n-SO_3^-M^+$$

wherein n is an integer from 2 to 5 inclusive and M+ is a physiologically acceptable alkaline earth metal cation or alkali metal cation.

6. The compound of claim 5 wherein n is 3 or 4 and M+ is selected from Na+, K+, ½ Ca++ and ½ Mg++.

7. The compound of claim 6 wherein n is 3 and M+ is Na+ or K+.

8. The compound of claim 3 wherein R is a 1 to 5 carbon inclusive alkyl polysulfonate.

9. The compound of claim 8 wherein R has the formula $$-(CH_2)-CH-(SO_3^-)_2M^+{}_2$$

M+ is a physiologically acceptable alkaline earth metal cation or alkali metal cation, and n is an integer of from 1 to 2 inclusive.

10. The compound of claim 3 wherein R is a 1 to 5 carbon atom alkyl terminal carboxylate of the formula $-(CH_2)_n-COO^-M^+$ and n is an integer from 1 to 5 inclusive and M+ is a physiologically acceptable alkaline earth metal cation or alkali metal cation.

11. The compound of claim 3 wherein R is an alkyl terminal phosphonate of the formula $-(CH_2)_n-PO_3H^- M^+$ and n is an integer from 1 through 5 inclusive and M+ is a physiologically acceptable alkaline earth metal cation or alkali metal cation.

12. The compound of claim 3 wherein R is a 1 through 5 carbon inclusive linear alkyl polycarboxylate.

13. The compound of claim 3 wherein R is a 1 through 5 carbon inclusive linear polyhydroxyl alkyl.

14. The compound of claim 3 wherein R is a 1 through 5 carbon inclusive primary alkyl amine salt.

15. The compound of claim 4 wherein R is a 1 through 5 carbon inclusive alkyl polysulfonate.

16. The compound of claim 3 wherein R is a 2 through 5 carbon inclusive alkyl amino carboxylate.

17. A sweet comestible comprising an edible material admixed with an effective sweetening amount of the compound of claim 1.

* * * * *